United States Patent

Samiotes et al.

[11] Patent Number: 5,256,157
[45] Date of Patent: Oct. 26, 1993

[54] AUTOMATED INFUSION PUMP WITH REPLACEABLE MEMORY CARTRIDGES

[75] Inventors: Nicholas Samiotes, Westwood; Donald Johanson, Wayland, both of Mass.; Paul Tamura, Seattle, Wash.

[73] Assignee: Baxter International Inc., Deerfield, Ill.

[21] Appl. No.: 989,949

[22] Filed: Dec. 10, 1992

Related U.S. Application Data

[63] Continuation of Ser. No. 648,600, Jan. 31, 1991.

[51] Int. Cl.5 .............................................. A61M 5/00
[52] U.S. Cl. ........................... 604/246; 128/DIG. 13; 604/151; 604/67
[58] Field of Search .............. 128/DIG. 12, DIG. 13; 604/245, 246, 251-255, 151-155, 65, 67

[56] References Cited

U.S. PATENT DOCUMENTS

| | | | |
|---|---|---|---|
| 4,270,532 | 6/1981 | Franetzki et al. | |
| 4,457,750 | 7/1984 | Hill | 604/65 |
| 4,676,776 | 6/1987 | Hawson | 604/66 |
| 4,838,857 | 6/1989 | Strowe et al. | 605/65 |
| 4,943,279 | 7/1990 | Samiotes et al. | 604/154 |
| 4,950,245 | 8/1990 | Braun et al. | 604/246 |
| 5,002,055 | 3/1991 | Merki et al. | 604/66 |
| 5,041,086 | 8/1991 | Koenig et al. | 604/65 |

FOREIGN PATENT DOCUMENTS

| | | |
|---|---|---|
| 0002775 | 7/1979 | European Pat. Off. . |
| 0188288 | 7/1986 | European Pat. Off. . |
| 655955 | 6/1988 | Switzerland . |

*Primary Examiner*—C. Fred Rosenbaum
*Assistant Examiner*—C. Smith
*Attorney, Agent, or Firm*—Kane, Dalsimer, Sullivan, Kurucz, Levy, Eisele & Richard

[57] ABSTRACT

An infusion pump system for dispensing a drug to a patient in accordance with a predetermined therapeutic modality, said system including a drug delivering member controlled by a microprocessor and replaceable memory modules coupled to said microprocessor for configuring specific pump user interface and other characteristics required for differing therapeutic modalities. Information specific to a particular patient is entered through input features on the pump.

9 Claims, 5 Drawing Sheets

AUTOMATED INFUSION PUMP WITH REPLACEABLE MEMORY CARTRIDGES

This is a continuation of copending application Ser. No. 07/648,600 filed on Jan. 31, 1991.

BACKGROUND OF THE INVENTION

A. Field of Invention

This invention pertains to a microprocessor controlled infusion pump for delivering drugs to a patient, and more particularly to an infusion pump with a memory cartridge which defines one of a variety of configurations for the pump, said cartridges being replaceable to allow the pump to be used in multiple, different environments.

B. Description of the Prior Art

Infusion pumps are used in the field of medicine to administer drugs to patients over an extended time period particularly durations longer than can be managed easily by direct injection. As availability of drugs, therapeutic techniques, and technological capability have improved, the demand for sophistication in drug delivery has increased. In many instances, this added sophistication results in more complicated device operation. Achieving this sophistication in drug delivery capability, and maintaining ease of use has been a major challenge for infusion pump manufacturers.

One reason that devices have become complicated is the breadth of drug dosing methods used. For example, such different modes of operation as Patient Controlled Analgesia (PCA) and physician interactive dosing for operating room infusions must somehow be accommodated. Other current therapy modes in use include continuous infusion, bolus plus continuous infusion, clinician interactive dosing, PCA with continuous infusion, time/dose, and multiple automatic time/dose.

Figure 1:
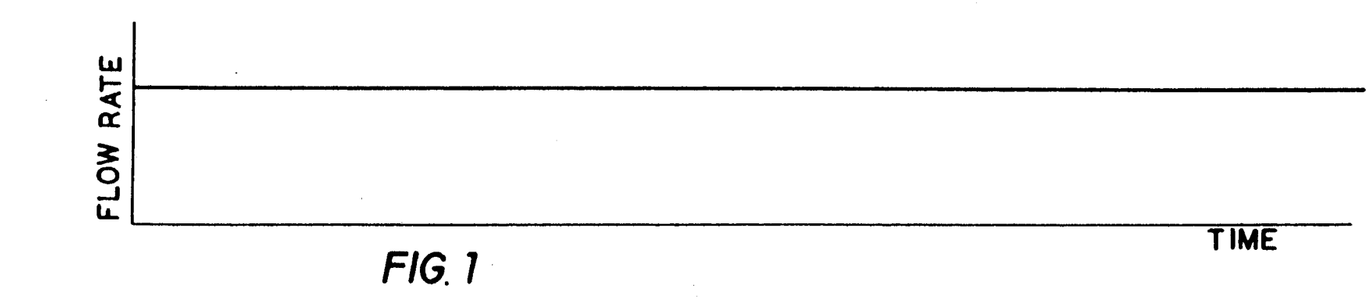
FIGS. 1-6 show time charts for various kinds of infusion that can be performed with an infusion pump constructed in accordance with this invention.

Continuous infusion is the most traditional method of drug delivery. FIG. 1 shows a graph of a constant drug flow vs. time. The infusion rate may be changed, if necessary, but whatever rate is selected will continue indefinitely. In this type of infusion, the user only selects the rate in ml/hr or drops/minute.

Figure 2:
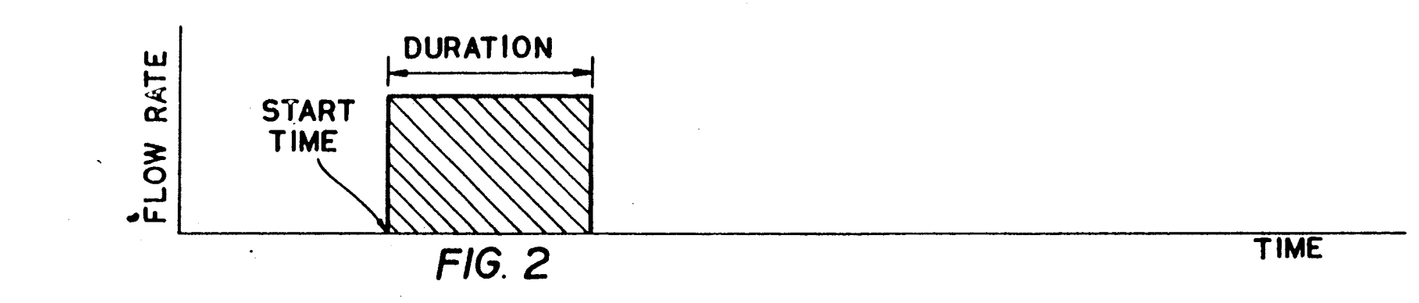

Time/dose therapy is shown in FIG. 2. This therapy is accomplished with a number of different devices for many different drugs. One device, a syringe infusion pump described in U.S. Pat. No. 4,544,369, has no rate input at all. The selection of syringe size and dose volume define the duration of infusion and, thus, the flow rate. Other devices have flow rate and dose volume as inputs. Still others require dose volume and duration of infusion as inputs. Intermittent medications such as antibiotics and H₂ agonists are often administered using these devices.

Figure 3:
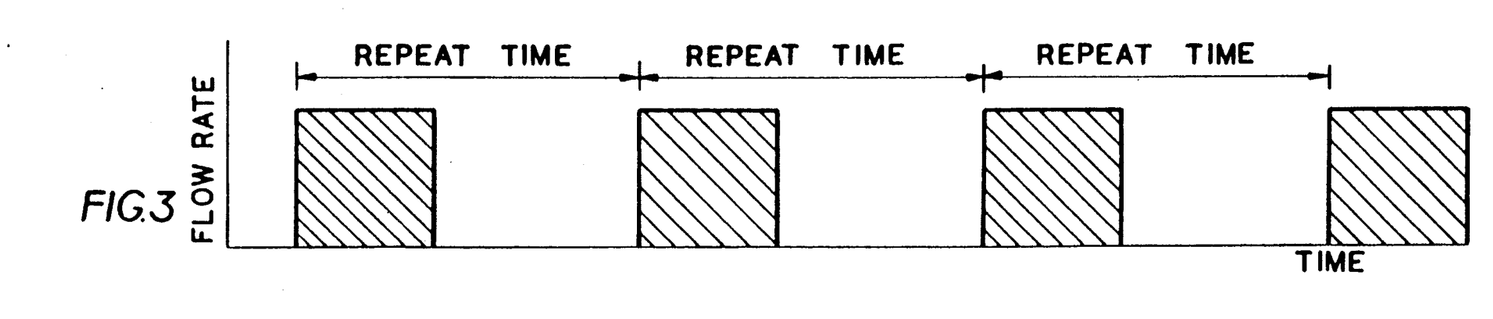

FIG. 3 shows a multiple dose scheme. This method is similar to time/dose, but also includes a repeat time as a user defined parameter. The pump automatically starts each dose at predetermined time intervals.

Figure 4:
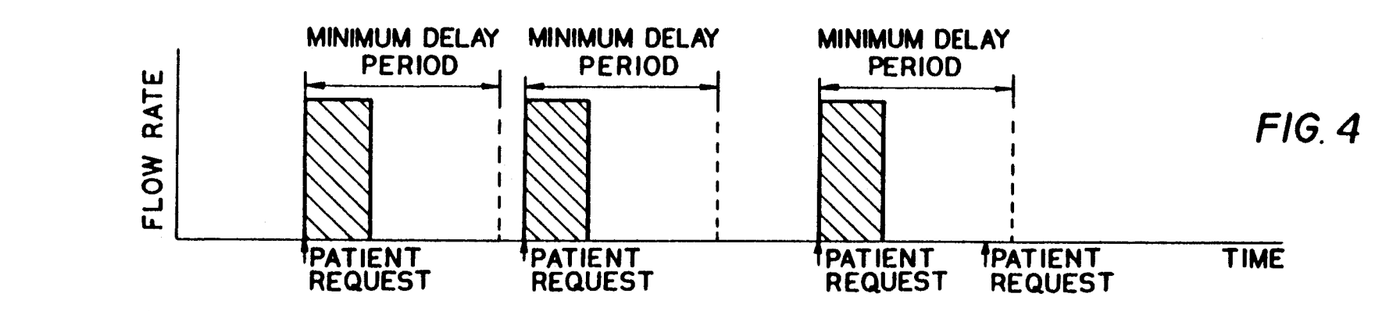

FIG. 4 shows patient controlled analgesia (PCA) therapy. The clinician typically selects a dose size, and a minimum delay or lockout period. The patient may request a drug dose using a bedside request button connected to the pump. The pump administers a dose only if it has been requested during the minimum time period after the administration of a previous dose.

Figure 5:
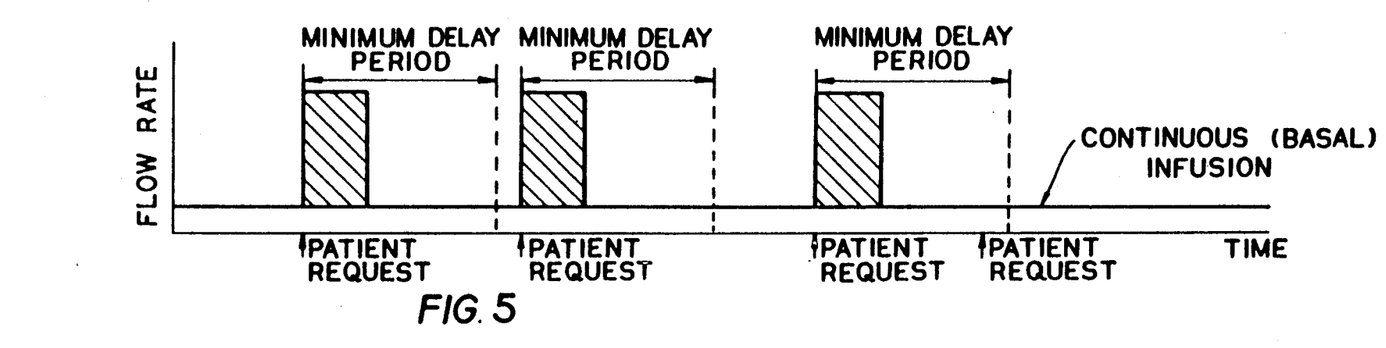

Often, a continuous infusion is superimposed over PCA therapy as shown in FIG. 5. The clinician must select a continuous infusion rate along with the dose size and minimum delay period. PCA therapy may also include additional clinician selectable features. These include a loading dose at the start of or during therapy and secondary prescription limits (e.g. hourly limit).

Figure 6:
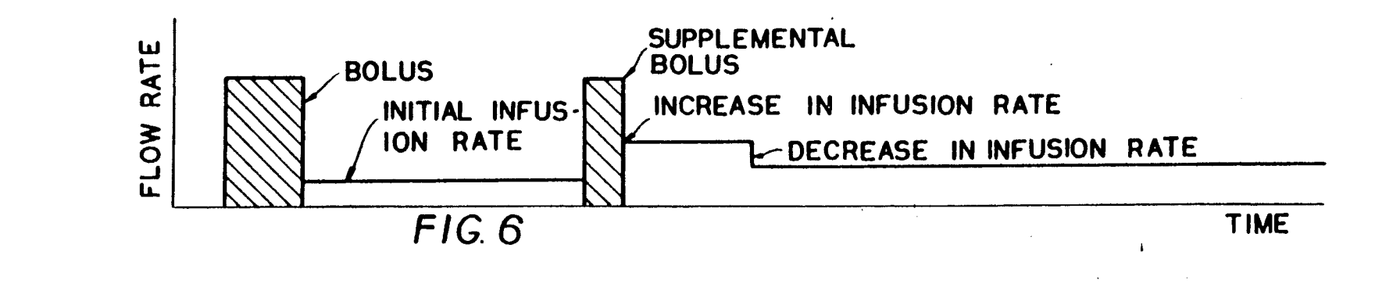

Interactive dosing is commonly done in the operating room (OR) or the intensive care unit (ICU). FIG. 6 shows a typical course of therapy. The clinician selects appropriate rates, boluses, and changes based on patient response or therapeutic goal. Aspects of interactive dosing are common to all infusion schemes because the actual dosing requirements change from patient to patient and from time to time. Nevertheless, certain circumstances require rapid interactive dosing not necessarily available or even desirable on all devices. An example of a device particularly well suited for this type of interactive dosing is made by C. R. Bard and is described in U.S. Pat. No. 4,943,279.

Of particular importance to the foregoing discussion is the wide variety of user selectable primary dosing inputs. The range of possible user inputs includes, but is not limited to, infusion rate, infusion duration, dose volume, lockout period, repeat period, bolus size, and bolus rate. Secondary inputs may include patient weight, patient sex, syringe size, container volume, security codes, drug units (e.g. milligrams), drug concentration, or even pharmacokinetic parameters.

In addition, not only are the clinician inputs numerous and variable, but the infusion pump's outputs are also extensive. History and status information unique to each therapy must be presented to the user in a clear manner.

The totality of inputs and outputs is termed the user interface. This user interface often has one most desirable features for a particular therapeutic modality.

Because of the large number of therapeutic modalities and the extensive number of possible required inputs and outputs, the challenge to manufacturers has been great. Users desire most a user interface with only a particular set of inputs and outputs pertinent to a particular therapy. On the other hand, great versatility is desired by both the manufacturers and the users. Users desire versatility so their pumps can perform many therapies. Manufacturers have the same desire because the economies of scale can be more easily realized.

The infusion industry has collectively responded to these needs in a number of ways. First, compromises in features are often accepted in the interest of having versatile, general or multi-purpose pumps. For example, users may sometimes select doses based on body weight and drug units, but often times this may not be current practice for some drugs. Therefore when necessary, users perform conversion calculations so that rates may be selected in ml/hr. These calculations are time consuming and are potential error sources. Another example is that continuous infusion modes may be used for time/dose infusions. The user must either time the infusion or rely on "end of container" alarms to appropriately terminate delivery.

An alternate to general purpose pumps has been devices designed specifically for only one drug or therapy. This has proven desirable for some widespread therapies. Users value the simple operation of these devices since they include only those features needed for a particular therapy. The disadvantage of these devices is their lack of versatility. They usually cannot perform widely differing therapies, nor can they accommodate therapy advance over time.

OBJECTIVES AND SUMMARY OF THE INVENTION

In view of the above-mentioned disadvantages of the prior art, it is an objective of the present invention to provide an infusion pump system with variable user interface characteristics.

A further objective is to provide an infusion pump system which may be operated as a pump having particular user interface characteristics by using a replaceable memory module.

Yet another objective is to provide a pump system with user interface means thereon for adjusting the operation of the system in accordance with the needs and requirements of a particular patient.

Other objectives and advantages of the invention shall become apparent from the following description.

Briefly, an infusion pump system constructed in accordance with this invention consists of a reservoir for holding a drug to be dispensed, drug delivery means for delivering the drug to a patient and control means for operating the drug delivery means. The control means includes a microprocessor which communicates with a replaceable memory module such as a cartridge. The memory cartridge is used to configure the infusion pump system, and particularly the control means, to a particular user interface and to particular functional characteristics. The control means further includes keypads, rotary knobs, or other means of inputting specific dosing or patient information to the microprocessor. The control means further still includes display, alarm, or other means for communicating with the user. The control means also provides operating and monitoring means indicative of the internal functions of the infusion pump.

DETAILED DESCRIPTION OF THE INVENTION

Figure 7:
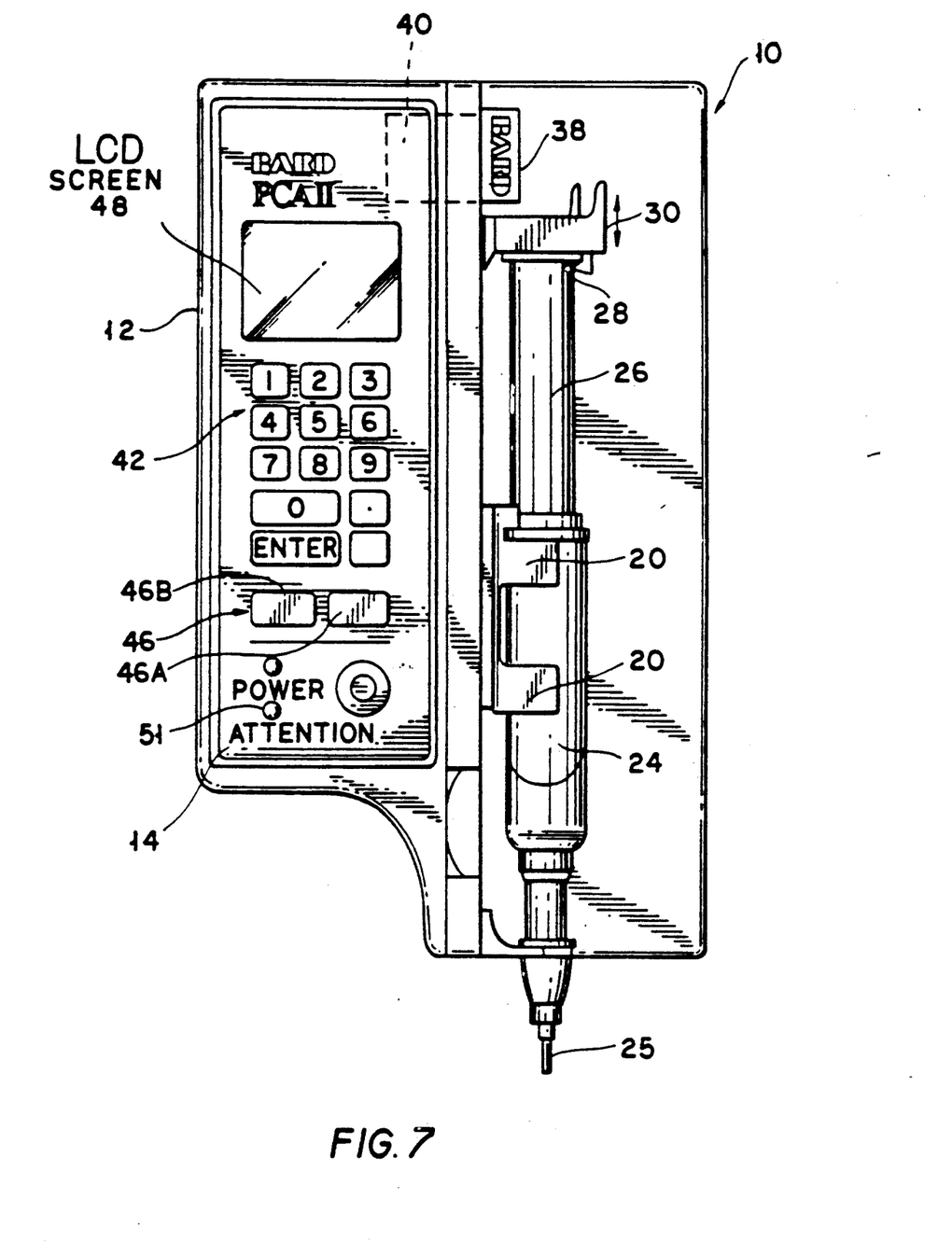
FIG. 7 shows an elevational view of an infusion pump constructed in accordance with this invention.

As shown in the Figures, and more particularly in FIG. 7 an infusion pump 10 may include a housing 12 with a front 14 used to hold various control and display means used to set up and operate the pump as described more fully below. The housing 12 may include mounting means (not shown) for securing the pump to an IV pole or another stationary frame.

On one side of the housing the pump is provided with a bracket 20, for engaging and holding the barrel 24 of a syringe. The bracket 20, may include sensors for sensing the diameter of syringe barrel 24. The syringe also includes a plunger 26 reciprocated in the barrel 24. The plunger 26 is terminated by a flange 28 which is captured by a plunger activating assembly 30. Assembly 30 is coupled to and driven by a motor (shown in FIG. 8) up or down to permit the plunger 26 to be inserted into or out of syringe barrel 24. Thus, in FIG. 7 the downward movement of assembly 30 causes the plunger 26 to eject the contents of the syringe barrel 24 either directly into the blood stream of a patient through a catheter device or into an IV through line 25. Therefore, the delivery of the drug from syringe barrel 24 to the patient is controllable through the vertical downwardly movement of the assembly 30 as well as the size of the syringe.

Figure 8:
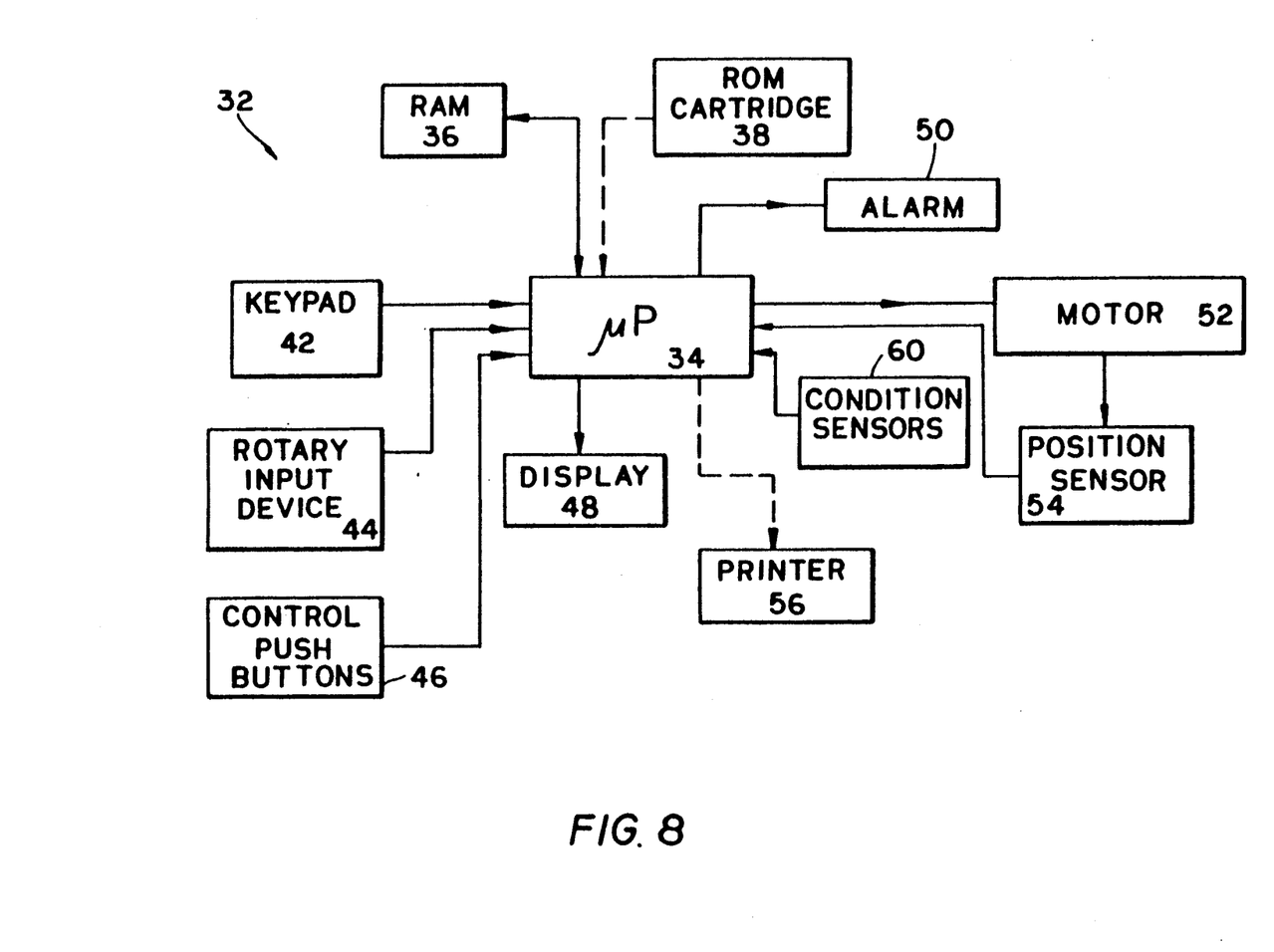
FIG. 8 shows a schematic diagram for the control of the infusion pump of FIG. 7.

Inside the housing 12, there is the motor mentioned above for driving assembly 30, and a control system 32 shown in more detail in FIG. 8. The control system 32 includes a microprocessor 34, which is coupled to a RAM 36 as well as several input and output devices. RAM 36 is the random access memory for the microprocessor and holds appropriate memory for the pump. Importantly, the system 34 also includes replaceable ROM cartridge 38. As shown in FIG. 7, the housing 12 has a slot 40 accessible from the outside for holding ROM cartridge 38 so that the ROM cartridge 38 is readily removable and replaceable with another cartridge. Instructions and patient specific data are provided to microprocessor 34 from a standard keypad 42 and some additional control push-buttons 46. All these input devices are mounted on the face 14 of housing 12 as shown in FIG. 7. In addition the system is also provided with a screen such as an LCD-type screen 48, and alarms, including attention light 51 used to indicate an abnormal pump operation. The size of barrel 24 is determined from condition sensors 60 which may be mounted in brackets 20, 22. Microprocessor 34 generates control signals to a mechanical which are used to drive motor 52 for activating the plunger. The position of motor 52 is sensed by a motor sensor 54 and sent back to the microprocessor for verification. Optionally, a printer interface may also be provided for printing data from the microprocessor 34 to an external printer 56.

The general operation of the infusion pump shall now be described. Initially, a ROM cartridge 38 corresponding to a specific delivery profile, such as one of the profiles shown in FIGS. 1-6, is loaded into slot 40. In other words a ROM 38 is provided for each specific user interface, thereby defining the characteristics of a dedicated pump. The microprocessor 34 reads this information from the cartridge 38. Next, the microprocessor provides operational instructions on LCD display 48 and, if necessary, requests patient-specific information. In other words, display 48 is used to request dosing inputs such as flow rate, dose size, patient weight, drug concentration, etc., as required. The display 48 may also be used to identify the cartridge inserted in slot 40, and other initial information such as the size of the barrel as determined by the sensors 60, thereby providing a further means to insure that the pump is operated properly and that the patient will receive the correct drug dose. The operator of the pump enters the requested information through the key pad 42. The remaining control push buttons 46 may be dedicated to other functions such as a review function (46A) during which the information provided to the microprocessor is reviewed prior to the operation of the pump, or to start or stop the pump, by activating push button 46B.

Once the requested information is entered, the microprocessor 34 adjusts the operational parameters for the pump to meet the requirements of the specific patient, and on command, for example, from push button 46B starts the infusion. The microprocessor monitors the operation of the pump on a continuous basis, and in case of a malfunction, it activates alarm light 51 and/or any other alarms 50.

To summarize, the pump 10 may be used for infusion using the characteristics/parameters corresponding to a specific user interface defined by cartridge 38 to act as a particular type of, or dedicated pump. The operational parameters and user interface of the pump, as well as the procedure for administering a particular drug are all stored in a cartridge 38. Patient specific information and other information, are provided to the microprocessor during an initialization phase via the input means provided on face 14. As desired, cartridge 38 may be changed to a different user interface to implement another pump having different operational parameters, for administering a different drug or therapy. In this manner a single type of infusion pump is used to emulate a large number of pumps. If technical advances and/or new regulations require a new infusion profile, the pump is easily reconfigured by providing an appropriate cartridge 38. Furthermore, the cartridges are easily installed in the field by personnel with no programming knowledge or capability.

Figure 9:
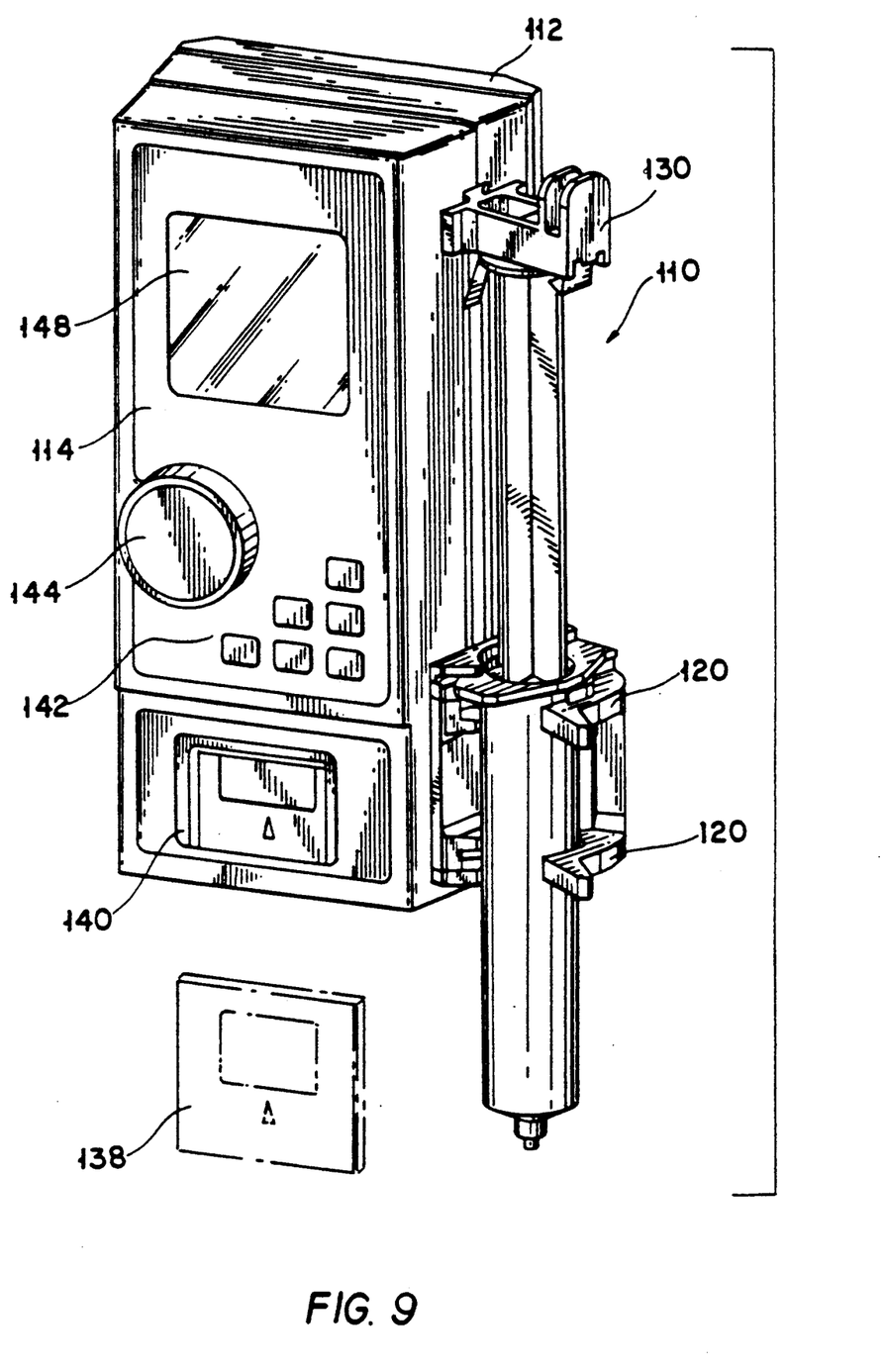
FIG. 9 shows an elevational view of an alternate embodiment of
the infusion pump.

FIG. 9 shows an alternate embodiment 110 of the infusion pump. Pump 110 includes housing 112 with bracket 120, disposed on one side with a corresponding plunger activating assembly 130. Housing 112 also has a face 114 with data entry and control push buttons 142, a rotary switch 144 and an LCD screen 148. Disposed below the key 142, there is a slot 140 for accepting a ROM cartridge 138. The operation of this embodiment is identical to the operation of the pump illustrated in types 7 and 8.

The infusion pump described herein has a number of benefits and advantages. A single pump may be used to serve multiple needs of a user in a single facility. The operation of the device is simplified since the instructions for setting up the pump for a particular operation are presented to the user one step at a time on the screen.

Existing applications, for example, to conform to changes in drug concentrations, acceptable usage, etc. may be easily updated without changing the pump. The pump can be easily configured for future applications.

Moreover, because each cartridge dedicates a pump to a specific pump configuration for each application, the pump is only as complicated as needed to perform those applications.

Software upgrades are easily implemented, thereby insuring greatly the pump's useful life.

The pump can be easily configured for special applications, thereby reducing development costs considerably.

The pump can be easily configured to accommodate new drugs and techniques.

Finally, a user is free to buy only the ROM cartridges for his specific application, with the option of buying more as required, or as they become available.

Obviously numerous modifications can be made to this invention without departing form its scope as defined in the appended claims.

I claim:

1. A universal infusion pump assembly wherein a single type of infusion pump is used to emulate a large number of different pumps, said assembly comprising:
 a. a single pump disposed in housing means for delivering a fluid to a patient;
 b. a set of replaceable memory modules, including a first and a second memory module, each memory module containing information including a program describing a non-patient specific user interface set, including operational parameters and a specific delivery profile characteristic of a respective dedicated pump;
 c. selection means mounted on said housing for generating patient-specific information for said patient; and
 d. microprocessor means associated with said housing for operating said single pump, said microprocessor means being coupled to one of said memory module, wherein when coupled to said first memory module, said microprocessor means reads said information from said first memory module and operates said single pump to emulate a first dedicated pump; and wherein said microprocessor means, when coupled to said second memory module, reads said information from said secondary memory module and reconfigures the single pump to emulate a second dedicated pump.

2. A universal infusion pump set for configuring a single infusion pump to mimic the operation of one of a plurality of dedicated infusion pumps, said set comprising:
 a. a housing means for positioning adjacent to a patient for delivering a fluid to said patient;
 b. reservoir means coupled to said housing for holding said fluid;
 c. delivery means for delivering said fluid to said patient from said reservoir;
 d. a set of memory modules, including a first memory module and a second memory module, each memory module containing a program describing a non-patient specific user interface set, including operational parameters and a specific delivery profile characteristic of a respective dedicated pump;
 e. input means mounted on said housing for inputting patient-specific information; and
 f. microprocessor means for controlling said delivery means, said microprocessor means being coupled to one of said memory modules, wherein said microprocessor means reads said program and said patient-specific information from said first memory modules and operates said delivery means in conformance with said user interface to emulate a first dedicated pump; and
 alternately wherein said microprocessor means reads information from said second memory module and operates said delivery means to emulate a second dedicated pump.

3. The system of claim 2 further comprising display means mounted on said housing for displaying output data from said microprocessor.

4. The system of claim 3 wherein said display means includes a display panel for displaying operational instructions.

5. The system of claim 3 wherein said display means includes an alarm indicator for indicating an abnormal operating condition.

6. The system of claim 2 further comprising manual control means mounted on said housing.

7. The system of claim 6 wherein said manual control means includes manual keys disposed on said housing.

8. A universal infusion pump assembly using a single pumping means configured to emulate one of a plurality of dedicated pumps, said assembly comprising:
 a. housing means for positioning adjacent to a patient for dispensing a fluid to said patient, said housing including a single delivery pump;

b. reservoir means coupled to said housing for holding said fluid;

c. a set of memory modules, including a first memory module and a second memory module, each memory module containing a program describing a non-patient specific user interface set, including operational parameters and a specific delivery profile characteristic of a respective dedicated pump;

d. a keypad having several keys selected by an operator for inputting patient-specific information; and e. pump control means for controlling said delivery pump, said control means including:
  (i) microprocessor means disposed in said housing for operating said delivery pump; and
  (ii) coupling means mounted on said housing for accepting one of said memory modules externally of said housing, wherein said microprocessor means when coupled to said first memory module, reads said program and said patient-specific information and operates said single delivery pump in conformance with said user interface set to emulate a first dedicated pump; and alternately wherein said microprocessor means when coupled to a second memory module reconfigures said single delivery pump to emulate a second dedicated pump.

9. A method of administering a drug to a patient comprising the steps of:

a. providing an infusion pump system having a reservoir with a drug, delivery system means for delivering said drug to a patient including drug pump means, delivery control means including a microprocessor for operating said delivery means and selection means for generating patient specific information for said patient, said pump means, said microprocessor and said selection means being disposed in a common housing, and a set of memory modules, including a first memory module and a second memory module, each module containing a program describing a non-patient specific user interface set, including operational parameters and a specific delivery profile characteristic of a respective dedicated pump;

b. selecting a specific memory module;

c. coupling said specific memory module to said microprocessor, wherein said microprocessor reads information defining said non-specific specific user interface; and d. generating patient specific information to said microprocessor through said selection means wherein said microprocessor operates said delivery system in conformance with said user interface to mimic a first dedicated pump when coupled to said first memory module, and wherein said microprocessor operates said delivery means to mimic a second dedicated pump when coupled to said second memory module.

* * * * *

UNITED STATES PATENT AND TRADEMARK OFFICE
CERTIFICATE OF CORRECTION

PATENT NO. : 5,256,157
DATED : October 26, 1993
INVENTOR(S) : Nicholas Samiotes, Donald Johanson, Paul Tamura It is certified that error appears in the above-identified patent and that said Letters Patent is hereby corrected as shown below:

Column 6, line 16, "secondary" should be
--second--.

Column 8, line 19, "non-specific" should be
--non-patient--.

Signed and Sealed this

Twelfth Day of April, 1994

Attest:

BRUCE LEHMAN

Attesting Officer        Commissioner of Patents and Trademarks